United States Patent [19]

Ryder

[11] Patent Number: 5,046,192
[45] Date of Patent: Sep. 10, 1991

[54] HEADSET SUN VISOR

[75] Inventor: Francis E. Ryder, Arab, Ala.

[73] Assignee: Ryder International Corporation, Arab, Ala.

[21] Appl. No.: 412,458

[22] Filed: Sep. 26, 1989

[51] Int. Cl.⁵ .......................... A61F 9/04; H04R 5/033
[52] U.S. Cl. .................................................. 2/12; 2/6; 2/209; 381/187; 455/351
[58] Field of Search ........................ 2/209, 10, 12, 423, 2/424, 6; 381/183, 187, 25; 379/430; 455/351

[56] References Cited

U.S. PATENT DOCUMENTS

| | | | |
|---|---|---|---|
| 2,342,377 | 2/1944 | Small | 2/12 |
| 2,434,076 | 1/1948 | Kilham | 2/10 |
| 3,430,261 | 3/1969 | Benner | 381/183 X |
| 3,858,242 | 1/1975 | Gooding | 2/10 |
| 4,575,875 | 3/1986 | Danson et al. | 2/10 X |
| 4,682,363 | 7/1987 | Goldfarb et al. | 381/187 X |
| 4,802,243 | 2/1989 | Griffiths | 2/6 |
| 4,856,089 | 8/1989 | Horton | 2/209 X |
| 4,856,116 | 8/1989 | Sullivan | 2/12 X |
| 4,864,619 | 9/1989 | Spates | 381/187 X |

FOREIGN PATENT DOCUMENTS 2338005  8/1977  France ...................................... 2/424

Primary Examiner—Peter Nerbun
Attorney, Agent, or Firm—Trexler, Bushnell, Giangiorgi & Blackstone, Ltd.

[57] ABSTRACT

A visor adapted for use with a headset worn on a person's head having a brim portion formed to wrap around the front of said person's head providing shielding from visually adverse conditions. The brim portion is formed with rearwardly extending portions which terminate in clips used to mount the visor to the headset. The visor is integrally formed of a suitable plastic providing necessary rigidity and flexibility characteristics. The design of the clips exploit the flexibility characteristics of the plastic to removably retain the visor on the headset without any additional fasteners or adhesives. The clip is formed of two generally parallelly aligned flanges with a headband receiving gap therebetween, one flange formed with a heel portion and a gap and the other flange formed with a stabilizing flange. A portion of the headset fits into the gap and is retained in the gap by the stabilizing flange on the opposing flange.

9 Claims, 2 Drawing Sheets

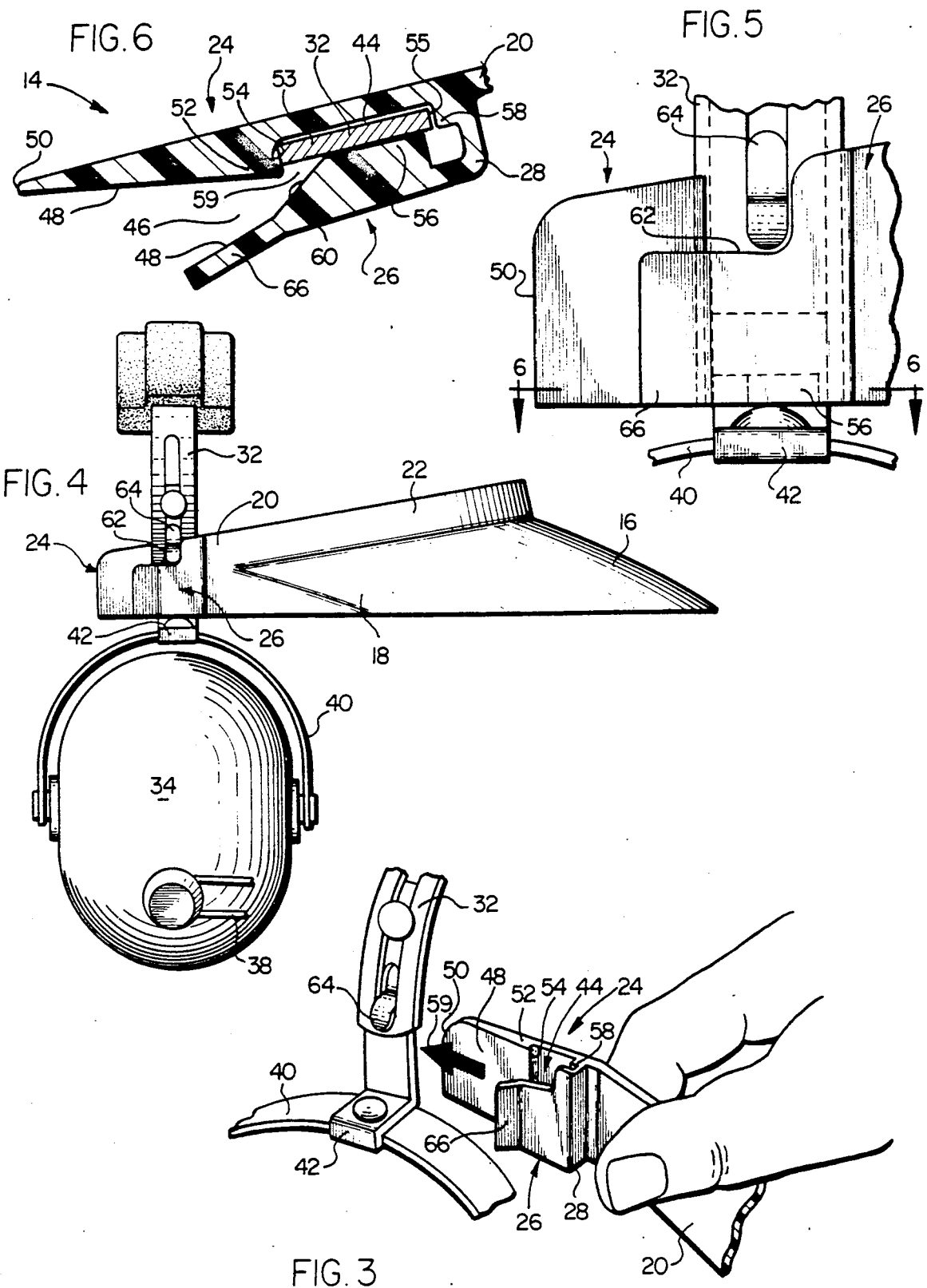

HEADSET SUN VISOR

BACKGROUND OF THE INVENTION

This invention relates generally to the visor arts and more particularly to a removably attachable visor adapted for use with a headset of the type employed in radio communications.

In many situations, such as private and commercial aviation, a visor is desirable to protect a person's eyes from visually adverse conditions such as direct sunlight, high intensity artificial light or reflected glare. The head gear or headsets to which the invention relates include, but are not limited to, radio communication headsets such as those used by pilots incorporating speakers mounted in the ear pieces with an attached boom condenser microphone worn over the head and hearing protection sets. Typically, when a conventional visor is used with a headset, the visor is worn over the headset, or the headset is worn over the visor. In this situation the visor may be in one of several forms such as a cap having a brim visor or a headband with an attached visor.

A problem with wearing a separate visor either over or under a headset is that the combination becomes cumbersome and uncomfortable after extended periods of wear. For example, with a cap worn under a headset the headset must be enlarged in order to accommodate the additional material of the cap and features of the cap often get pressed into the wearers head causing discomfort. In order to wear a cap over the headset the cap must be greatly enlarged to accommodate the headband of the headset and any additional equipment which may be mounted thereto.

When a visor mounted to a headband or the like is used in conjunction with a headset, the headband worn over the headset may excessively compress the ear covering portion of the headset against the users head and/or ears causing discomfort or, when worn under the headset, may flex the headband of the headset outwardly causing improper seating of the headset over the users head. Furthermore, when the visor is worn under a headset the headset must be removed each time the visor is removed. As an additional matter, when a user desires to temporarily reposition a portion of the headset, such as removing one ear piece while leaving one ear piece on, the visor worn under or over the headset is displaced since it is not an integral part of the headset.

OBJECTS AND SUMMARY OF THE INVENTION

A general object of the present invention is to provide a sun visor attachment adapted for use with a headset which removably attaches to the headset.

Another object of the present invention is to provide a sun visor attachment which is a unitary, one-piece body integrally formed of plastic.

Yet another object of the present invention is to provide a sun visor which has integrally formed clips which removably retain the visor on the headset.

Yet another object of the present invention is to provide a sun visor which is easily attached or removed from a headset without fasteners.

Briefly, and in accordance with the forgoing, the present invention comprises a novel sun visor which is removably attachable to a headset The visor is a unitary, one-piece, body integrally formed of plastic having a degree of flexibility permitting it to adapt to various types and sizes of headsets Integrally formed with the sun visor are clip means which permit the visor to be easily attached or removed from a headset. The clip means include a heel portion formed on one flange and a stabilizing flange formed on an opposing flange, the heel portion and stabilizing flange cooperatively engage a portion of the headset such as the headband to retain the sun visor thereon.

BRIEF DESCRIPTION OF THE DRAWINGS

The organization and manner of operation of the invention, together with the further objects and advantages thereof, may best be understood by reference to the following description taken in connection with the accompanying drawings in which like reference numerals identify like elements, and in which:

FIG. 3 is an enlarged partial perspective view of clip means integrally formed with the sun visor in position to be attached to the headband portion of the headset;

FIG. 4 is a side elevational view of the sun visor attached to a headband portion of the headset;

FIG. 5 is an enlarged partial side view of the clip means retainably engaged with the headband portion of the headset; and FIG. 6 is a cross-sectional view taken along the line 6—6 as shown in FIG. 5 illustrating the cooperative engagement of a heel portion and a stabilizing flange retaining a portion of the headband in engagement with the clip means.

DETAILED DESCRIPTION OF THE ILLUSTRATED EMBODIMENT

Figure 1:
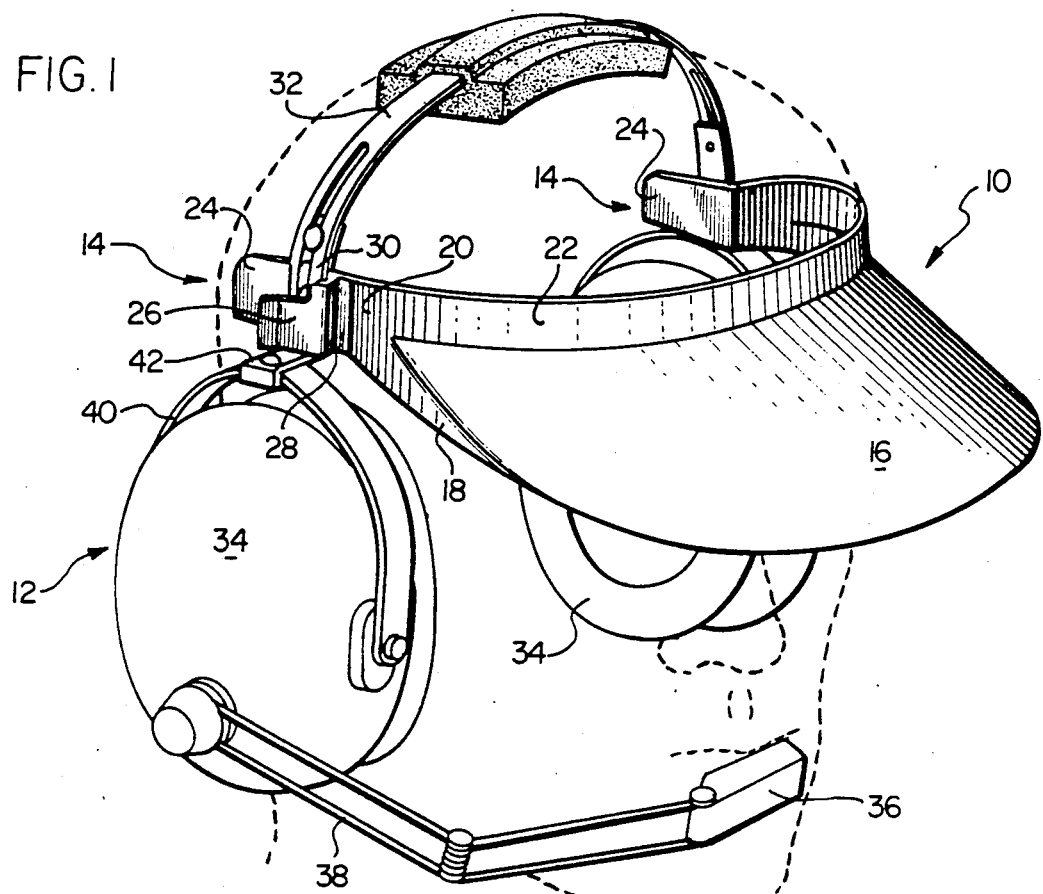
FIG. 1 is a perspective view of a sun visor attached to a headband portion of a headset as worn on a persons head (the persons head being indicated by ghost lines)

While this invention is susceptible to embodiment in many different forms, there is shown in the drawings and will be herein described in detail, one specific embodiment with the understanding that the present disclosure is to be considered an exemplification of the principles of the invention, and is not intended to limit the invention to the embodiment illustrated.

It should be noted that dimensional relationships between members of the illustrated embodiment may vary in practice or may have been varied in the illustrations to emphasize certain features of the invention.

FIG. 1 provides a perspective view of a visor 10 attached to a headset 12 by integrally formed clip means 14. The visor 10 is of a molded one-piece construction formed with a brim portion 16, rearwardly extending side portions 18 on each side of the brim 16, hanger or extension portions 20 generally formed between the rearwardly extending portions 18 and the clip means 14. A top rim 22 generally extends from an inside flange 24 of one clip means 14 around the top of the brim 16 to the other inside flange 24 of the other clip means 14. An outside flange 26 extends away from the top rim 22 on a flexible elbow 28.

The visor 10 is snappingly engaged with the side portions 30 of an adjustable headband 32 of the headset 12. It should be noted that typically a speaker cord or set of speaker wires is attached to and follows the head band 32 and the clip means 14 attaches to the head band 32 underneath any cords or wires For clarity in describing the present invention, the cords or wires have been deleted from the drawings. Generally, a headset 12 as illustrated in FIG. 1 has at least one ear portion or piece 34 which fits over the user's ear to block extraneous noise and in the illustrated embodiment includes a small radio speaker (not shown), with a microphone 36 extending from the headset 12 on a microphone boom arm 38. The ear portions 34 are typically mounted on a gimbal 40 which attaches to the headband 32 by a gimbal hanger 42. The headset 12, as shown in FIG. 1, has a pair of ear portions 34, 34 of which, the inside of the wearer's left ear portion and the outside of the wearer's right ear portion are illustrated.

When mounted to the headband 32, the visor 10 shields the wearer's eyes from visually adverse conditions. The brim 16 is generally formed integral with the top rim 22 in a inclined curve shape arching forwardly and slightly downwardly away from and over the wearer's forehead. A smooth curve is traced around the top of the wearer's head by the top rim 22 terminating at the clip means 14 which are directed slightly outwardly away from the wearer's head instead of following the curve of the top rim 22. No additional fasteners are necessary to mount the visor 10 to the headband 32; retention of the visor 10 to the headband 32 is accomplished entirely by the clip means 14.

Figure 2:
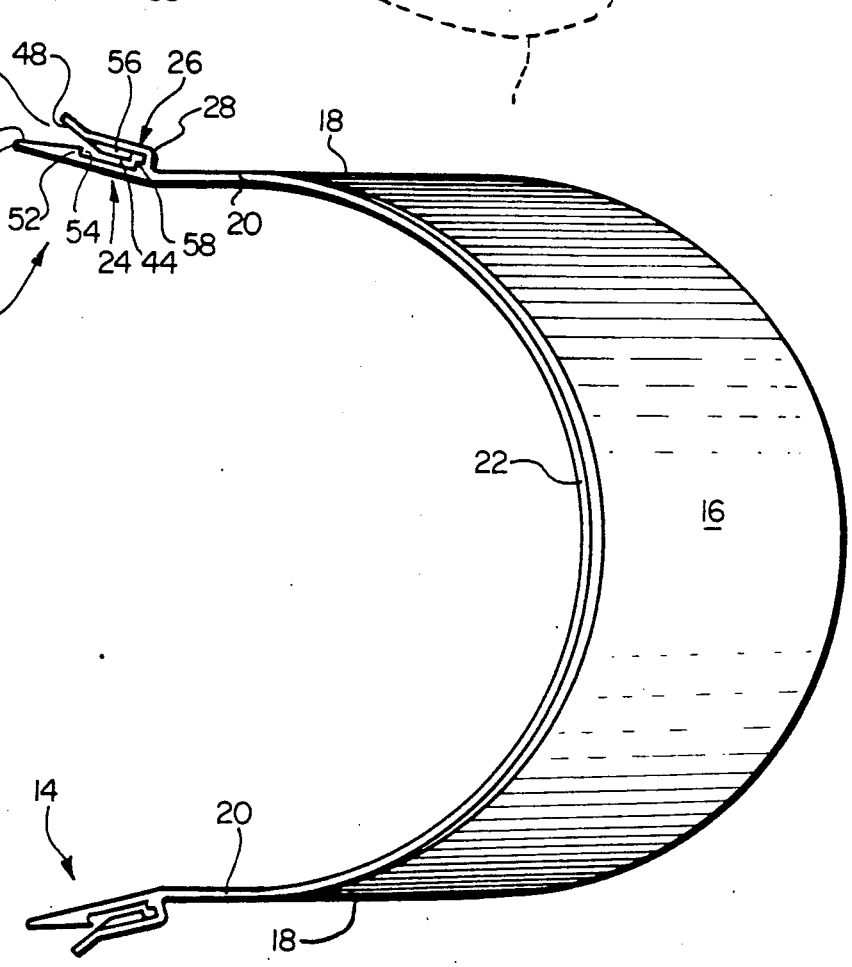
FIG. 2 is a top view of the sun visor shown in FIG. 1 detached from the headband portion of the headset.

FIG. 2 provides a top view of the visor 10 absent the headband 32 to which it attaches. As shown in FIG. 2, the clip means 14 formed on each side of the visor 10 at the rearwardly extending end of the extension portions 20, are angled slightly outwardly away from the inside of the top rim 22. The outward angle of the clip means 14 prevent additional compression of the headband 32. Further, such angling of the clip means 14 prevents pressing the inside flange 24 against the wearer's head.

The side portions 18 comprise an area providing a transition between the hanger or extension portions 20 and the rearwardly curving brim 16 and top portion 22. The side portions 18 are a generally rearwardly downwardly curving portion of the visor 10 providing wrap around shielding which further protects the wearer's eyes from adverse conditions While the top rim 22 is generally flexible, permitting removal of the headset with the visor 10 attached, it provides rigidity to the otherwise generally flexible brim 16.

As shown in FIG. 2, and in greater detail in FIG. 6, the clip means 14 provide several structural configurations which releasably retain the visor 10 to the headband 32. The inside flange 24 and the outside flange 26 are aligned generally parallel with a headband receiving gap 44 formed therebetween. The mouth 46 of the headband receiving gap 44 is formed with guiding edges or extensions 48 which are outwardly flared edges formed on the gap facing edges of the inside flange 24 and the outside flange 26 to facilitate insertion of the headband 32 into the gap 44.

The outside flange 26 is joined to the visor 10 by the flexible elbow 28. The rearwardly most extending portion of the inside flange 24 has a toe 50 from which the guiding edge 48 angles inwardly towards the gap 44 forming a heel portion 52 which retains one edge of the headband 32. While a back edge 53 of the headband 32 is retained in a heel recess 54 formed on the inside of the heel portion 52, a front edge 55 of the headband is retained against a headband stop or stabilizer projection 56 formed generally inwardly from the flexible elbow 28. A headband stabilizing flange 58 is formed on the inwardly facing surface of the outside flange to retain the headband 32 in the gap 44 and cooperate with the stop or projection 56 to minimize movement of the visor 10 relative to the head band 32.

FIG. 3 provides an enlarged partial perspective view which illustrates the attachment of one of the clip means 14 to the headband 32. As shown in FIG. 3, the visor 10 is gripped by the hanger or extension portion 20 and directed towards the headband portion 32 applying an engaging force (as indicated by arrow 59) thereto to engage the clip means 14 with the headband 32. The headband 32 is inserted into the mouth 46 of the gap 44 formed between the guiding edges 48 of the inside flange 24 and the outside flange 26. As better illustrated in FIG. 6, a space 59 between the heel 52 and a sloped edge 60 of the stabilizing flange 58 is generally relatively smaller than the thickness of the headband 32 and forms a sharp angle which must be overcome to insert the headband 32 into the gap 44. However, since the clip means 14 is integrally formed of a generally flexible resilient plastic, exerting pressure on the clip means 14 held as shown in FIG. 3, forces the outside flange 26 to flex sufficiently outwardly to permit the headband 32 to enter the gap 44, with the structure of the clip means 14 tending to return to its original configuration to grip the head band 32 firmly between flanges 24 and 26.

FIG. 4 provides a side view of the visor 10 retained on the headset 12. FIG. 5 provides an enlarged view of the area of the headband 32 where the clip means 14 retains the visor 10 on the headset 12. As shown in FIG. 5, a top edge portion of the outer flange is removed to provide a recess 62 to accommodate a headband adjustment stop or protrusion 64. Recess 62 does not impair the retaining abilities of the clip means 14 since the stabilizing flange 58 is formed generally along the bottom edge of the outside flange 26. However, if a headband adjustment stop 64 does not interfere with the clip means 14, such a recess 62 need not be formed in the outer flange 26.

FIG. 6 provides a cross sectional view of the clip means 14 taken along the line 6—6 as illustrated in FIG. 5. The cross section of FIG. 6 provides an enlarged view of the clip means 14 as discussed hereinabove in reference to FIG. 2. A cross section of the headband 32 is shown to be retained within the gap 44 between the stop 58 and the heel recess 54. The stop 58 and the heel recess 54, which extend vertically through the inside flange 24 as shown in FIG. 5, prevent the visor 10 from moving upwardly or downwardly and securely retains the horizontal orientation of the visor brim 16 once mounted on the headband 32 thus providing greater stability of the visor 10. The stabilizing flange 56 presses the headband 52 into the gap 44 thereby preventing detachment of the visor 10 from the headband.

In order to remove the visor from the headband, the inside flange 24 and the outside flange 26 must be forced apart to open the mouth 46 of the headband receiving gap 44 providing a wide enough space to permit passage of the headband 32 therethrough. The extended toe 50 of the inside flange 24 and an outside flange tab 66, which is a general extension of the outside flange 26, provide additional leverage to overcome the flexible retaining forces inherent in the plastic utilized in forming the clip means 14. Forcing the inside flange 24 away from the outside flange 26 generally results in greater flexion of the outside flange 26 at the flexible elbow 28. Once the two flanges 24, 26, are forced sufficiently apart, the headband 32 is urged away from the gap 44 utilizing slight pressure to release the back edge 53 of the headband 32 from the heel recess 54. The procedure described above is repeated to remove the other clip means 14 from the other side of the headband 32.

It should be noted that where circumstances require, the visor 10 described above can be formed with a single clip means 14 to retain the visor 10 to a headband or similar structure Such a circumstance may arise in using a single ear piece headset such that the user may still desire the beneficial protection of the visor 10, but the equipment may not accommodate a double clip visor 10 as herein illustrated above. Further, depending upon the type of head gear to which the visor 10 is to be mounted, the clip means 14 can be positioned on other portions of the visor 10 other than a rearwardly extending extension portion 20 as illustrated. Additionally, the clip means 14 can be configured as necessary to accommodate head bands of different design or construction, without departing from the spirit and scope of the invention.

While a preferred embodiment of the present invention is shown and described, it is envisioned that those skilled in the art may devise various modifications of the present invention without departing from the spirit and scope of the appended claims.

The invention is claimed as follows:

1. A visor attachable to a headband portion of a headset worn on a person's head, said headband portion having an inside surface facing said person's head and an outside surface directed away from said person's head, said visor comprising: a brim portion formed to wrap around the front of a person's head for shielding a person's eyes from visually adverse conditions, two rearwardly extending portions integrally formed with said brim portion, said rearwardly extending portions being formed at angles directed outwardly away from each other for preventing said visor from creating compressive forces on a headset to which it is attached; a clip member attached to an end of each of said rearwardly extending portions distal said brim portion for releasably attaching said visor to said headband of said headset in a fixed position.

2. A visor attachable to a headband portion of a headset worn on a person's head, said headband portion having an inside surface facing a person's head and an outside surface directed away therefrom, said visor comprising: a brim portion formed to wrap around the front of a person's head for shielding a person's eyes from visually adverse conditions, said brim portion having two rearwardly extending portions; a clip member attached to an end of each of said rearwardly extending portions distal said brim portion for releasably attaching said visor to said headband of said headset in a fixed position; an inside flange and an outside flange formed on said clip member, said inside and outside flanges being engagable with inside and outside surfaces of a headband, said flanges being joined at one end and attached to said rearwardly extending portions, a headband receiving gap being formed between said flanges for receiving a headband of a headset for attaching said visor thereto; guiding edges formed on at least one of said inside and outside flanges of said clip member along the surface of said headband receiving gap facing said headband, said guiding edges angling inwardly towards said headband receiving gap for guiding a headband positioned thereagainst into engagement with said clip member when an engaging force is applied thereto; edges formed on said inside and outside flanges flaring outwardly from said headband receiving gap for receiving said headband for promoting insertion of said headband therein; a stabilizing flange being formed generally perpendicularly on a surface of one of said inside and outside flanges, said surface facing said headband receiving gap, said stabilizing flange compressibly engaging a headband for fixedly retaining a headband between said inside and outside flanges.

3. A visor for use with a headset having a headband positioned over a person's head for wearing thereon, said visor comprising: a brim portion projecting in front of a person's head having side portions extending rearwardly therefrom, said side portions being formed at divering angles directed outwardly away from one another; a clip member integrally formed with said visor for removably attaching said visor to a headband of a headset, said clip member comprising an inside flange and an outside flange, said inside and outside flanges being integrally formed with said side portions of said visor, said flanges having formed therebetween a headband receiving gap into which said headband is inserted to attach said visor thereto; a guiding edge formed on one of said inside and outside flanges of said clip member being angled for guiding a headband positioned thereagainst into releasable engagement with said clip member when an attaching force is applied to said clip member and said headband; a stabilizing flange being formed on one of said inside and outside flanges on a surface facing a headband receiving gap, said stabilizing flange generally formed perpendicular to one of said inside and outside flanges and having an angularly formed edge facing an open portion of a headband receiving gap for receiving a headband when inserted into said headband receiving gap, a headband being compressibly retained between an abutting surface of said stabilizing flange and a surface of the other of said inside and outside flanges facing said headband receiving gap for retaining said visor in a fixed position relative to said headband.

4. A visor for use with a headset worn on a person's head, said headset having a headband positioned over said person's head, said visor comprising an integrally formed flexible plastic brim portion, two rearwardly extending portions, and a clip member, said brim portion projecting in front of and generally wrapping around a portion of the sides of a person's head, said rearwardly extending portions integrally formed with said brim portion and extending towards a headband of a headset, said clip member integrally formed on the end of said rearwardly extending portions for releasably attaching said visor to a headset in a fixed position; said clip member comprising an inside flange and an outside flange, said flanges integrally formed and biasedly deflectable relative to one another and being at one end of each said rearwardly extending portions, a headband receiving gap being formed between said inside and outside flanges for receiving a headband therein, guiding edges being formed on one of said inside and outside flanges and being angled for guiding a headband positioned thereagainst into said headband receiving gap when an attaching force is applied thereto; a projecting heal portion being formed on one of said inside and outside flanges facing inwardly towards said headband receiving gap for releasably retaining a headband within said headband receiving gap once engaged therewith.

5. A visor releasably attachable to a headband portion of a headset worn on a person's head, the headband portion of the headset having an inside surface facing a person's head on which it is worn and an outside surface facing an opposite direction, the headband portion of the headset extends over the top of a person's head in an arch, said visor comprising: a brim portion projecting in front of a person's head being formed with two side portions extending rearwardly therefrom for attachment to said headband portion for shielding a person's eyes from visually adverse conditions; a clip member including two flanges being integrally formed on the ends of each of said side portions for removably attaching said visor to a headband of a headset, said two flanges extending rearwardly from each of said side portions, said clip member compressibly retaining a headband extending transverse thereto and engaged therein for retaining said visor in a fixed position on a headband portion.

6. A visor according to claim 7, wherein said clip member is formed with inside and outside flanges, said inside and outside flanges being engagable with inside and outside surfaces of a headband respectively, said flanges being joined at one end and attached to each of said rearwardly extending portions, and defining a headband receiving gap formed between said inside and outside flanges for receiving a headband of a headset inserted therein.

7. A visor releasably attachable to a headband portion of a headset worn on a person's head, the headband portion of the headset having an inside surface facing a person's head on which it is worn and an outside surface facing an opposite direction, said visor comprising: a brim portion projecting in front of a person's head being formed with two side portions extending rearwardly therefrom for attachment to said headband portion such that said visor, when attached to a headband, shields a person's eyes from visually adverse conditions, said side portions extending rearwardly from said brim portion are formed at diverging angles for preventing said visor from creating compressive forces in a headband of a headset to which it is attached; a clip member integrally formed on the ends of said side portions for removably attaching said visor to a headband of a headset, said clip member compressibly retaining a headband engaged therein for retaining said visor in a fixed position on a headband portion.

8. A visor releasably attachable to a headband portion of a headset worn on a person's head, the headband portion of the headset having an inside surface facing a person's head on which it is worn and an outside surface facing an opposite direction, said visor comprising: a brim portion projecting in front of a person's head being formed with two side portions extending rearwardly therefrom for attachment to said headband portion such that said visor, when attached to a headband, will shield a person's eyes from visually adverse conditions; a clip member integrally formed on the ends of said side portions for removably attaching said visor to a headband of a headset, said clip member compressibly retaining a headband engaged therein for retaining said visor in a fixed position on a headband portion, said clip member is formed with inside and outside flanges, said inside and outside flanges being engagable with inside and outside surfaces of a headband respectively, said flanges being joined at one end and attached to each of said rearwardly extending portions, and defining a headband receiving gap formed between said inside and outside flanges for receiving a headband of a headset inserted therein, a stabilizing flange formed on one of said flanges and a projecting heel portion formed on the other of said inside and outside flanges, said stabilizing flange and projecting heel portion facing inwardly towards said headband receiving gap and engaging a headband inserted therein for cooperatively retaining said headband within said clip means for removably attaching said visor to a headband in a fixed position.

9. A visor according to claim 5, wherein each said clip member includes a pair of flange members, one said flange member defining a gap for receiving said headband portion, the other of said flange members overlying said gap to maintain said headband portion therein to thus retain said visor in a fixed position on said headband portion.

* * * * *

UNITED STATES PATENT AND TRADEMARK OFFICE
CERTIFICATE OF CORRECTION

PATENT NO. : 5,046,192
DATED : September 10, 1991
INVENTOR(S) : Francis E. Ryder It is certified that error appears in the above-identified patent and that said Letters Patent is hereby corrected as shown below:

Column 6, Line 12 "divering angles" it should read -- diverging angles --

Column 7, Line 16 "A visor according to claim 7," it should read

-- A visor according to claim 5,--

Signed and Sealed this

Second Day of March, 1993

*Attest:*

STEPHEN G. KUNIN

*Attesting Officer*  *Acting Commissioner of Patents and Trademarks*